United States Patent
Wiggins et al.

(10) Patent No.: US 9,794,705 B2
(45) Date of Patent: *Oct. 17, 2017

(54) HEARING AID TUNING SYSTEM AND METHOD

(71) Applicant: Bowie-Wiggins LLC, Burien, WA (US)

(72) Inventors: Dan Wiggins, Edmonds, WA (US); Don Bowie, Burien, WA (US)

(73) Assignee: Bowie-Wiggins LLC, Burien, WA (US)

( * ) Notice: Subject to any disclaimer, the term of this patent is extended or adjusted under 35 U.S.C. 154(b) by 49 days.

This patent is subject to a terminal disclaimer.

(21) Appl. No.: 14/504,328

(22) Filed: Oct. 1, 2014

(65) Prior Publication Data

US 2015/0016621 A1  Jan. 15, 2015

Related U.S. Application Data

(63) Continuation of application No. 13/889,217, filed on May 7, 2013, now Pat. No. 8,867,764, which is a continuation of application No. 12/760,435, filed on Apr. 14, 2010, now Pat. No. 8,437,486.

(60) Provisional application No. 61/169,242, filed on Apr. 14, 2009.

(51) Int. Cl.
| | |
|---|---|
| H04R 25/00 | (2006.01) |
| A61B 5/12 | (2006.01) |
| G06F 3/0484 | (2013.01) |

(52) U.S. Cl.
CPC ............. *H04R 25/70* (2013.01); *A61B 5/121* (2013.01); *G06F 3/0484* (2013.01); *H04R 25/305* (2013.01); *H04R 2225/55* (2013.01)

(58) Field of Classification Search
CPC ...... H04R 25/00; H04R 25/70; H04R 25/305; H04R 2225/55; G06F 3/0484; A61B 5/121
USPC ............... 381/60, 23.1, 312, 314, 320, 321; 600/559
See application file for complete search history.

(56) References Cited

U.S. PATENT DOCUMENTS

| | | | | |
|---|---|---|---|---|
| 7,450,724 B1* | 11/2008 | Greminger | ............ | H04R 25/70 381/312 |
| 7,627,127 B2* | 12/2009 | Aida | ............ | H04R 25/70 381/314 |
| 8,107,655 B1* | 1/2012 | Howes | ............ | H04R 25/552 381/312 |
| 2003/0133578 A1* | 7/2003 | Durant | ............ | G06N 3/126 381/60 |
| 2007/0255435 A1* | 11/2007 | Cohen | ............ | H04R 1/1016 700/94 |
| 2008/0056518 A1* | 3/2008 | Burrows | ............ | H04R 25/70 381/314 |
| 2009/0154741 A1* | 6/2009 | Woods | ............ | H04R 25/70 381/312 |

* cited by examiner

*Primary Examiner* — Melur Ramakrishnaiah
(74) *Attorney, Agent, or Firm* — AEON Law, PLLC; Adam L.K. Philipp; Jonathan E. Olson

(57) ABSTRACT

Systems and methods are provided herein that provide for hearing aid tuning.

15 Claims, 16 Drawing Sheets

HEARING AID TUNING SYSTEM AND METHOD

CROSS-REFERENCE TO RELATED APPLICATIONS

This application is a continuation of U.S. Non-Provisional patent application Ser. No. 13/889,217; filed May 7, 2013; titled HEURISTIC HEARING AID TUNING SYSTEM AND METHOD; and naming inventors Dan WIGGINS et al. U.S. Non-Provisional patent application Ser. No. 13/889,217 is a continuation of U.S. Non-Provisional patent application Ser. No. 12/760,435 (now U.S. Pat. No. 8,437,486); filed Apr. 14, 2010; titled CALIBRATED HEARING AID TUNING APPLIANCE; and naming inventors Dan Wiggins et al. U.S. Non-Provisional patent application Ser. No. 12/760,435 (now U.S. Pat. No. 8,437,486) claims the benefit of priority to U.S. Provisional Patent Application No. 61/169,242; filed Apr. 14, 2009; titled CALIBRATED HEARING AID TUNING APPLIANCE; and naming inventors Dan Wiggins et al. The above-cited applications are hereby incorporated by reference, in their entireties, for all purposes. The following disclosure was originally incorporated by reference into U.S. Non-Provisional patent application Ser. No. 13/889,217.

FIELD

This disclosure relates generally to hearing aids, and more specifically, to systems and methods for hearing aid tuning.

BACKGROUND

At some point in their lives, many people may experience a hearing impairment, a full or partial decrease in their ability to detect or understand sounds. For many such hard of hearing individuals, the degree of hearing impairment varies by sound frequency. For example, many hard of hearing individuals may have little or no impairment at low sound frequencies, but varying degrees of impairment at higher frequencies. Loss of the ability to understand speech is generally regarded as one of the more detrimental aspects of hearing impairment. The frequency range from about 100 Hz-8 kHz is generally regarded as being useful for understanding speech.

In some cases, certain groups of hard of hearing individuals may share certain general characteristics. For example, statistical thresholds of hearing have been developed for men and women of various ages. However, most individuals have a distinct pattern of impairment that may vary from the statistical thresholds. Consequently, devices that are intended to compensate for an individual's personal hearing impairment often perform better when they are matched to the individual's distinct pattern of impairment.

Many hearing aids include several filters covering different parts of the audible frequency spectrum. By adjusting the response of the several filters, a hearing aid can often be "tuned" to compensate for an individual's distinct pattern of impairment.

At the present time, hearing aids are generally tuned by an auditory healthcare professional, often in a clinical setting. As part of the tuning process, an audiogram (a standardized plot representing the individual's hearing threshold) may be created, generally by performing a "pure tone audiometry" hearing test. Pure tone audiometry hearing tests usually involve presenting pure tones at varying frequencies and levels to an individual wearing calibrated headphones in a sound-controlled environment. The resulting audiogram may provide a starting point for tuning a hearing aid, but it is generally regarded that pure tone audiometry may not accurately measure an individual's perception of his or her hearing impairment. For example, pure tone audiometry may not be able to accurately measure the effect of "dead regions" in an individual's basilar membrane. In addition, pure tone audiometry may not measure various factors that are important to speech intelligibility.

Consequently, a further step in tuning a hearing aid generally includes asking the hearing aid wearer to subjectively evaluate speech. Often, the auditory healthcare professional will use his or her own voice as a test signal, speaking words or phrases and asking the hearing aid wearer to evaluate the spoken words or phrases. In many cases, the spoken words may include words selected from several pairs of words that differ only by an initial, final, or intervocalic consonant. The auditory healthcare professional may then use the individual's responses to adjust various hearing aid filter parameters.

However, this approach to speech intelligibility tuning may have drawbacks. For example, it may be difficult to achieve consistent results from tuning session to tuning session. In many cases, a hearing aid may need to be tuned multiple times, often over a period of days or weeks, before the wearer finds its performance acceptable. In many cases, the auditory healthcare professional's voice may change slightly or significantly from session to session (e.g., the professional's voice may be altered when he or she has a cold), so it may be difficult to compare results from session to session. In other cases, an auditory healthcare professional may retire or move, in which case, speech intelligibility may be evaluated based on a completely different voice.

BRIEF DESCRIPTION OF THE DRAWINGS

The present disclosure will be presented by way of exemplary embodiments but not limitations, illustrated in the accompanying drawings in which like references denote similar elements, and in which.

DESCRIPTION

Illustrative embodiments presented herein include, but are not limited to, systems and methods for hearing aid tuning.

Various aspects of the illustrative embodiments will be described using terms commonly employed by those skilled in the art to convey the substance of their work to others skilled in the art. However, it will be apparent to those skilled in the art that the embodiments described herein may be practiced with only some of the described aspects. For purposes of explanation, specific numbers, materials and configurations are set forth in order to provide a thorough understanding of the illustrative embodiments. However, it will be apparent to one skilled in the art that the embodiments described herein may be practiced without the specific details. In other instances, well-known features are omitted or simplified in order not to obscure the illustrative embodiments.

Further, various operations and/or communications will be described as multiple discrete operations and/or communications, in turn, in a manner that is most helpful in understanding the embodiments described herein; however, the order of description should not be construed as to imply that these operations and/or communications are necessarily order dependent. In particular, these operations and/or communications need not be performed in the order of presentation.

The phrase "in one embodiment" is used repeatedly. The phrase generally does not refer to the same embodiment; however, it may. The terms "comprising," "having" and "including" are synonymous, unless the context dictates otherwise.

The following disclosure relates to a hearing aid tuning system 100, which may allow a hearing aid user 105 to tune hearing aids 130A-B while being worn by a user 105. A calibrated tuning device 200 may present various audio stimuli to the user 105, and the user's 105 response to the audio stimuli can be interpreted to determine how the hearing aids 130A-B should be tuned.

Figure 1:
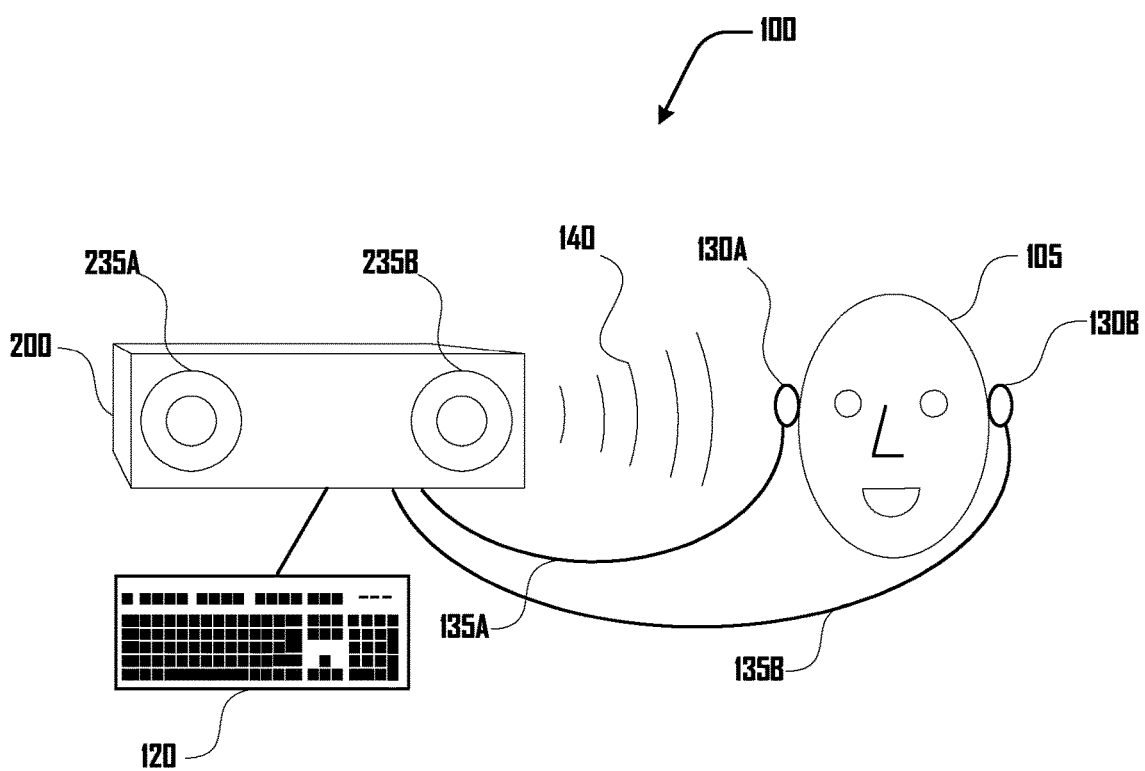
FIG. 1 is a pictorial diagram of a system of interconnected devices, in accordance with various embodiments.

FIG. 1 depicts an exemplary hearing aid tuning system 100, which comprises a tuning device 200. The tuning device 200 comprises calibrated transducers 235A-B, an input device 120, and a first and second coupling body 135A-B. The first and second coupling body 135A-B are operable to couple with and facilitate communication with a first and second hearing aid 130A-B, which may be worn by a user 105.

In some embodiments, the first and second coupling body 135A-B may couple via a magnet, a slot and pin, and the like. Additionally, communication between the tuning device 200 and the first and second hearing aid 130A-B may be achieved via digital or analog signals, which may be communicated via an inductive connection, direct wire connection, wireless connection, and the like. In further embodiments, the first and second coupling body 135A-B, may selectively couple with one of the first and second hearing aid 130A-B, which may have a left-ear or right-ear orientation.

In one embodiment, tuning device 200 is coupled to one or more hearing aid 130A-B via a magnetic-inductive data coupler, as described in U.S. Pat. No. 8,363,872 entitled "MAGNETIC EARPIECE COUPLING SYSTEM," with inventors Daniel Wiggins and Donald Bowie, which is hereby fully incorporated by reference in its entirety.

In various embodiments the tuning device 200 may comprise an input device 120, which may be a keyboard (as shown in FIG. 1). Alternatively, in some embodiments, various buttons may be present on the tuning device 200, or the input device 120 may be a mouse, trackball, or the like. In further embodiments, the tuning device 200 may comprise a display 240 (see FIG. 2), which may facilitate tuning, user input, and the like. In some embodiments, the tuning device 200 may be in communication with a host computing device (not shown) which may comprise a display, input device 120, and the like.

In one embodiment, a tuning device 200 or calibrated tuning appliance may be as described in U.S. Pat. No. 8,437,486, titled "CALIBRATED HEARING AID TUNING APPLIANCE", with inventors Daniel Wiggins and Donald Bowie, which is hereby fully incorporated by reference.

In some embodiments, the tuning device 200 may present an audio stimulus via sound waves 140 to a user 105 wearing, or not wearing, hearing aids 130A-B, and the user 105 may perceive the audio stimulus via the hearing aids 130A-B and/or via the user's natural hearing. The user 105 may then indicate a response to the audio stimulus via the input device 120. The user's response may be used to determine whether a hearing aid settings should be modified, and the tuning device 200 may then program one or both of the hearing aids 130A-B via the first and/or second coupling body 135A-B.

Figure 2:
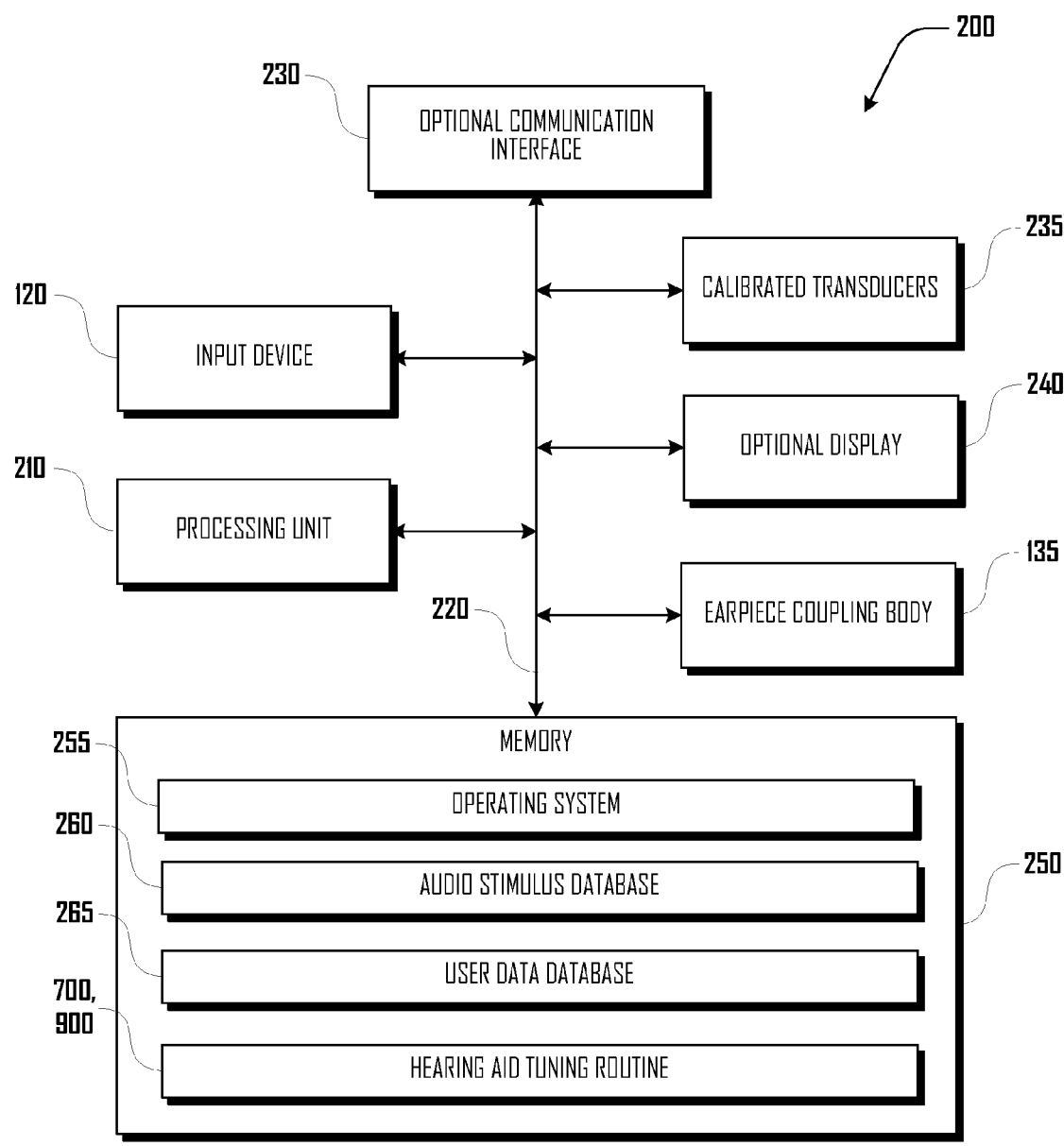
FIG. 2 is a block diagram of a device that provides an exemplary operating environment for various embodiments.

FIG. 2 illustrates several components of an exemplary tuning device 200 for an embodiment. In alternate embodiments, the tuning device 200 may include many more components than those shown in FIG. 2. However, it is not necessary that all of these generally conventional components be shown in order to disclose an enabling embodiment for practicing the embodiments described herein.

As shown in FIG. 2, the tuning device 200 includes an optional communication interface 230 for connecting to a host device or to other remote devices (not shown). The communication interface 230 may be a network interface designed to support a local area network ("LAN"), wireless local area network ("WLAN"), personal area network ("PAN"), Worldwide Interoperability for Microwave Access ("WiMax"), telephone network, pager network, powerline connection, serial bus, IEEE-1394 bus (i.e., "FireWire"), universal serial bus ("USB") wireless connection, or the like. The communication interface 230 includes the necessary circuitry, driver and/or transceiver for such a connection and is constructed for use with the appropriate protocols for such a connection. In some embodiments, a host device or other remote device (not shown) may provide power and/or input/output capability to tuning device 200.

The tuning device 200 also includes a processing unit 210, an optional display 240, calibrated transducers 235, and input device 120, an earpiece coupling body 135, and a memory 250, all interconnected along with the communication interface 230 via a bus 220. Display 240 may not be necessary in all forms of a tuning device 200, and, accordingly, display 240 is an optional component. In some embodiments, display 240 may be provided by an optional host device (not shown) via communication interface 230. The memory 250 generally comprises random access memory ("RAM"), a read only memory ("ROM") and a permanent mass storage device, such as a disk drive, flash RAM, or the like.

The memory 250 stores the program code necessary for a hearing aid tuning routing 700, 900. Additionally, the memory 250 stores an operating system 255, an audio stimulus database 260, and a user data database 265.

Various software components may be loaded from a computer readable medium into memory 250 of the tuning device 200 using a drive mechanism (not shown) or network mechanism (not shown) associated with the computer readable medium, such as a floppy, tape, digital video disc (DVD)/CD-ROM drive, flash RAM, network interface card, or the like.

Although an exemplary tuning device 200 has been described that generally conforms to a conventional general-purpose computing device, a tuning device 200 may be any of a great number of devices capable of functioning as such a device, server or operating environment that is within the spirit or scope of the embodiments described herein or can perform at least one function of the embodiments described herein.

In some embodiments, various other devices can configure or interact with the tuning device 200 using a graphical user interface. An example of a graphical user interface is an interactive web page, e.g., in HTML (HyperText Markup Language), Flash, JavaScript, VBScript, JScript, ASP.NET, PHP (HTML Preprocessor) or XHTML (eXtensible HyperText Markup Language) form, or the like.

Figure 3:
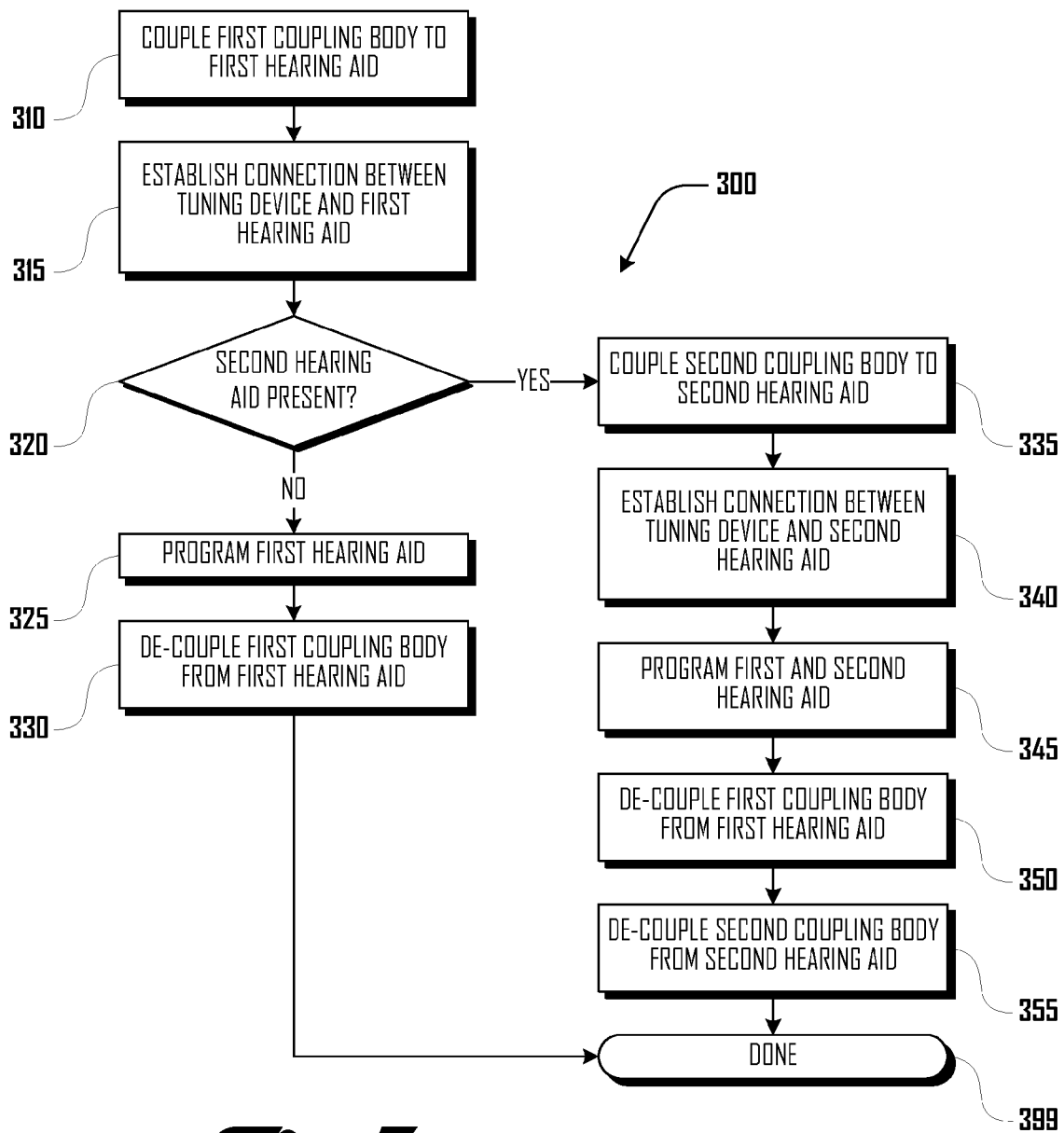
FIG. 3 is a flow diagram illustrating a hearing aid coupling and programming routine in accordance with various embodiments.

FIG. 3 is a flow diagram illustrating a hearing aid coupling and programming routine 300 in accordance with various embodiments. As depicted in FIG. 3, the hearing aid coupling and programming routine 300 begins in block 310 where a first coupling body 135A is coupled to a first hearing aid 130A. In block 315 a connection is established between the tuning device 200 and a first hearing aid 130A.

As discussed herein, coupling may be achieved in various ways, which may include one or more of magnet coupling, a friction fit of slot and pin, and the like. For example, see U.S. Pat. No. 8,363,872, entitled "MAGNETIC EARPIECE COUPLING SYSTEM," with inventors Daniel Wiggins and Donald Bowie, which is fully incorporated by reference in its entirety.

Additionally, communication between the tuning device 200 and first hearing aid 130A may be achieved in various ways, including direct wire connection, a wireless connection, an inductive connection, and the like. As used herein, a connection between the tuning device 200 and a hearing aid 130 may comprise an operable data connection which allows the tuning device 200 to program a hearing aid 130 and otherwise obtain, modify, update, erase hearing aid data, and the like.

The hearing aid coupling and programming routine 300 continues to decision block 320 where a determination is made whether a second hearing aid 130B is present. If a second hearing aid 130B is present, the hearing aid coupling and programming routine continues to block 335, where a second coupling body 135B is coupled to the second hearing aid 130B and in block 340 a connection is established between the tuning device 200 and the second hearing aid 130B.

In block 345, the first and second hearing aid 130A-B are programmed, and in block 350, the first coupling body 135A is decoupled from the first hearing aid 130A. In block 355, the second coupling body 135B is decoupled from the second hearing aid 130B, and the hearing aid coupling and programming routine 300 ends in block 399.

However, if in decision block 320 a determination is made that a second hearing aid 130B is not present, the hearing aid coupling and programming routine 300 continues to block 325, where the first hearing aid 130A is programmed. In block 330, the first coupling body 135A is decoupled from first hearing aid 130A, and the hearing aid coupling and programming routine 300 ends in block 399.

Figure 4:
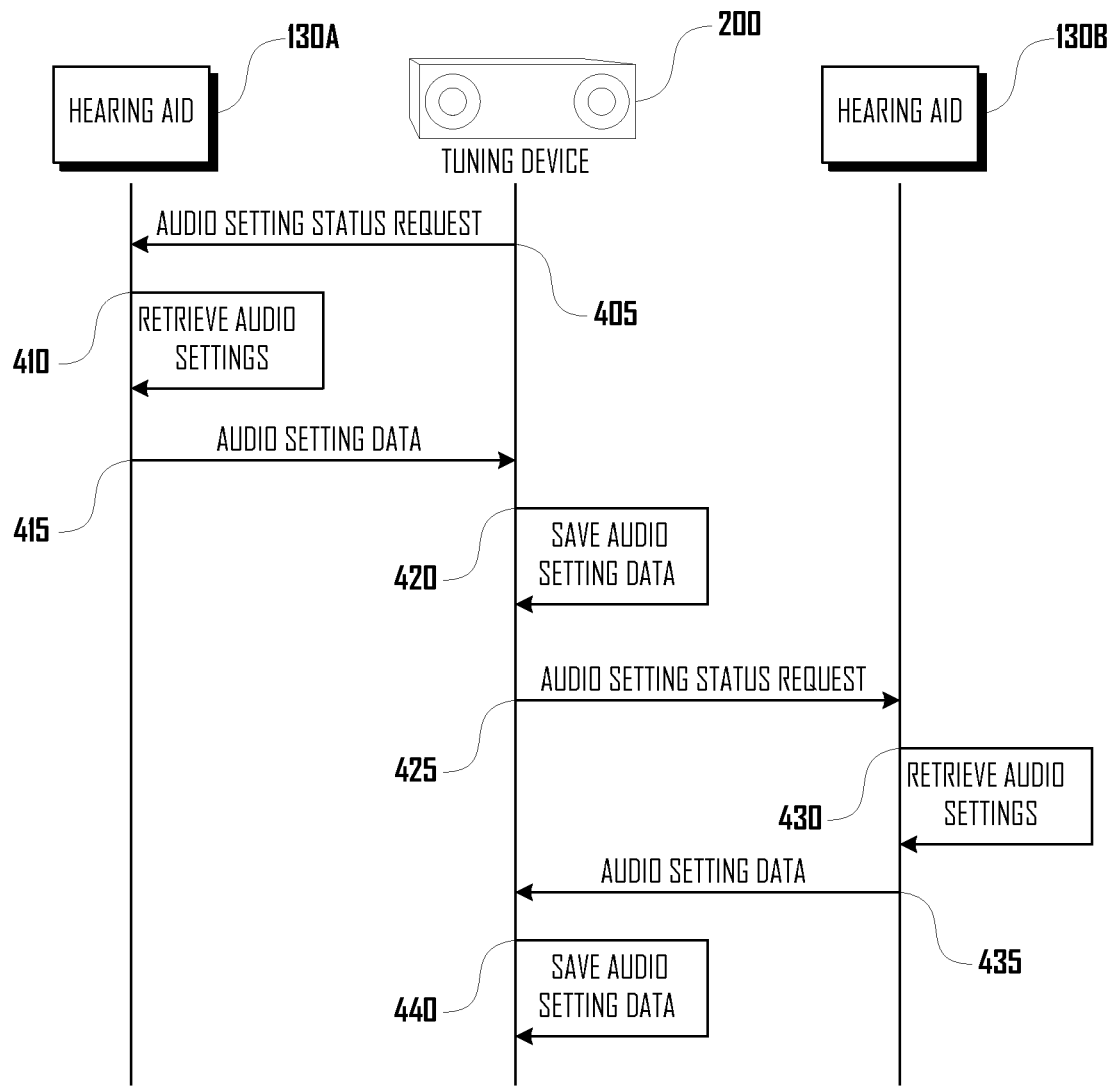
FIG. 4 is a diagram illustrating the actions taken by a first and second hearing aid and a tuning device in accordance with various embodiments.

FIG. 4 is a diagram illustrating the actions taken by a first and second hearing aid 130A-B and a tuning device 200 in accordance with various embodiments. The actions begin where an audio setting status request is sent 405 to the first hearing aid 130A, where audio settings are retrieved 410. Audio setting data is sent 415 to the tuning device 200, where audio setting data is saved 420. The tuning device 200 sends 425 a setting status request to the second hearing aid 130B, which retrieves 430 audio settings. Audio setting data is sent 435 to the tuning device 200, which saves 440 audio setting data.

In some embodiments, it may be desirable to obtain the setting of a first and second hearing aid 130A-B, as illustrated in FIG. 4, because the initial settings of the hearing aids 130A-B may be relevant to subsequent changes that may be made to hearing aid settings. Furthermore, initial hearing aid settings may be saved so that the hearing aid may be re-set to these settings if desired by a user 105. Hearing aid settings may be saved in a user data database 265.

For example, in various embodiments, a first and second hearing aid 130A-B may be associated with a right or left ear of a user 105, and the user's 105 hearing capabilities in the right and left ear may be different. Accordingly, the hearing aid settings of the hearing aid 130A-B for each ear may be different, and settings into both hearing aids 130A-B may be changed in relation to these different settings.

For example, a first hearing aid 130A may have an equalization filter centered at 1 kHz with gain of 5 db and a second hearing aid 130B may have an equalization filter centered at 1 kHz with a gain of 7 db. If a determination is made that the gain of the 1 kHz equalization filters should be increased by 1 db, then this increase may be in relation to the initial settings of 5 db and 7 db. Accordingly the first hearing aid 130A may be set to a gain of 6 db for the equalization filter at 1 kHz and the second hearing aid 130B may be reset to a gain of 8 db for the equalization filter at 1 kHz. Additionally, more that one setting group (memory/program) may be present within a hearing aid and knowledge and/or location of each may be relevant.

In alternate embodiments, first and second hearing aid 130A-B may not respond to a status request 405, 425. In such embodiments, initial hearing aid settings may be unavailable. In other embodiments, initial hearing aid settings may be retrieved from user data database 265 (or from another data store) without sending status requests 405, 425 to first and second hearing aids 130A-B. In some embodiments, the actions illustrated in FIG. 4 may not be take place.

Figure 5:
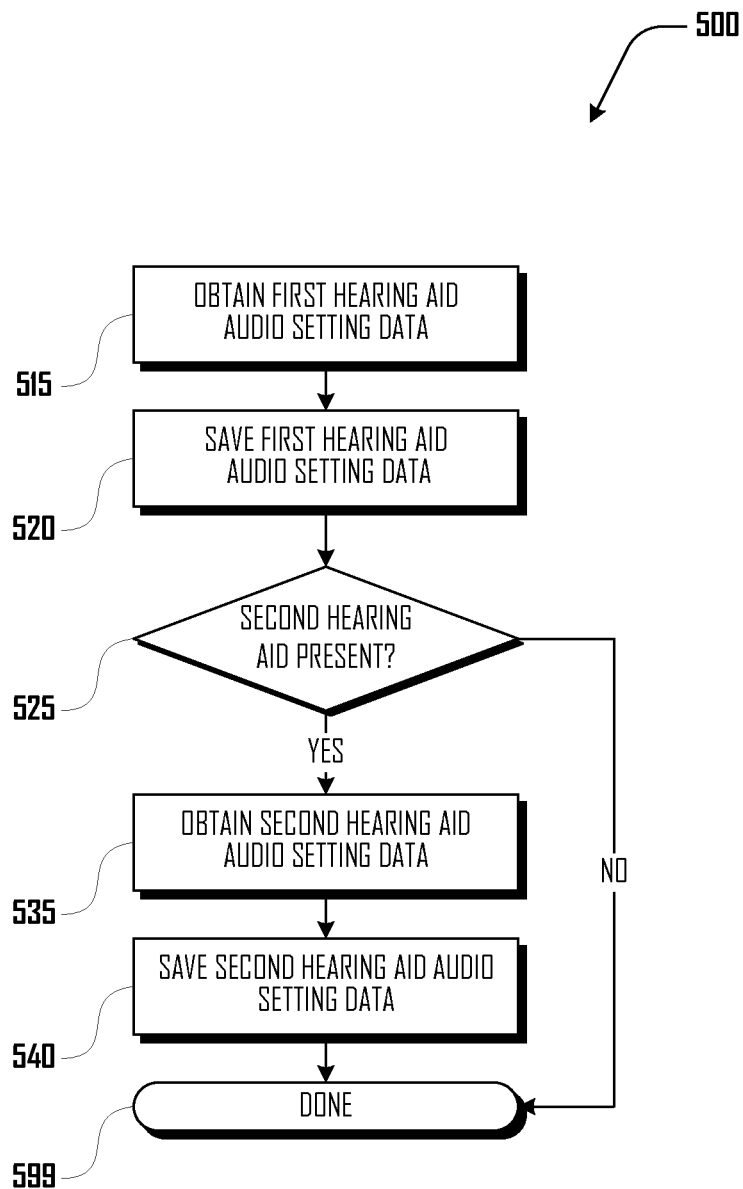
FIG. 5 is a flow diagram illustrating an audio setting obtaining routine in accordance with various embodiments.

FIG. 5 is a flow diagram illustrating an audio setting obtaining routine 500 in accordance with various embodiments. The audio setting obtaining routine 500 begins in block 515, where first hearing aid audio setting data is obtained. In block 520, first hearing aid audio setting data is saved. In decision block 525 a determination is made whether a second hearing aid is present. If a second hearing aid is not present, the audio setting obtaining routine 500 ends in block 599. However, if in decision block 525 a second hearing aid is determined to be present, the audio setting obtaining routine 500 continues to block 535, where second hearing aid audio setting data is obtained. In block 540, second hearing aid audio setting data is saved, and the audio setting obtaining routine 500 ends in block 599.

In some embodiments, obtaining hearing aid audio data settings, as in blocks 515 and 535, may comprise querying first and/or second hearing aid 130A-B, as illustrated in FIG. 4. In other embodiments, obtaining hearing aid audio data settings, as in blocks 515 and 535, may comprise retrieving settings from user data database 265 or from another data store. In some embodiments, audio setting obtaining routine 500 may not be utilized.

Figure 6:
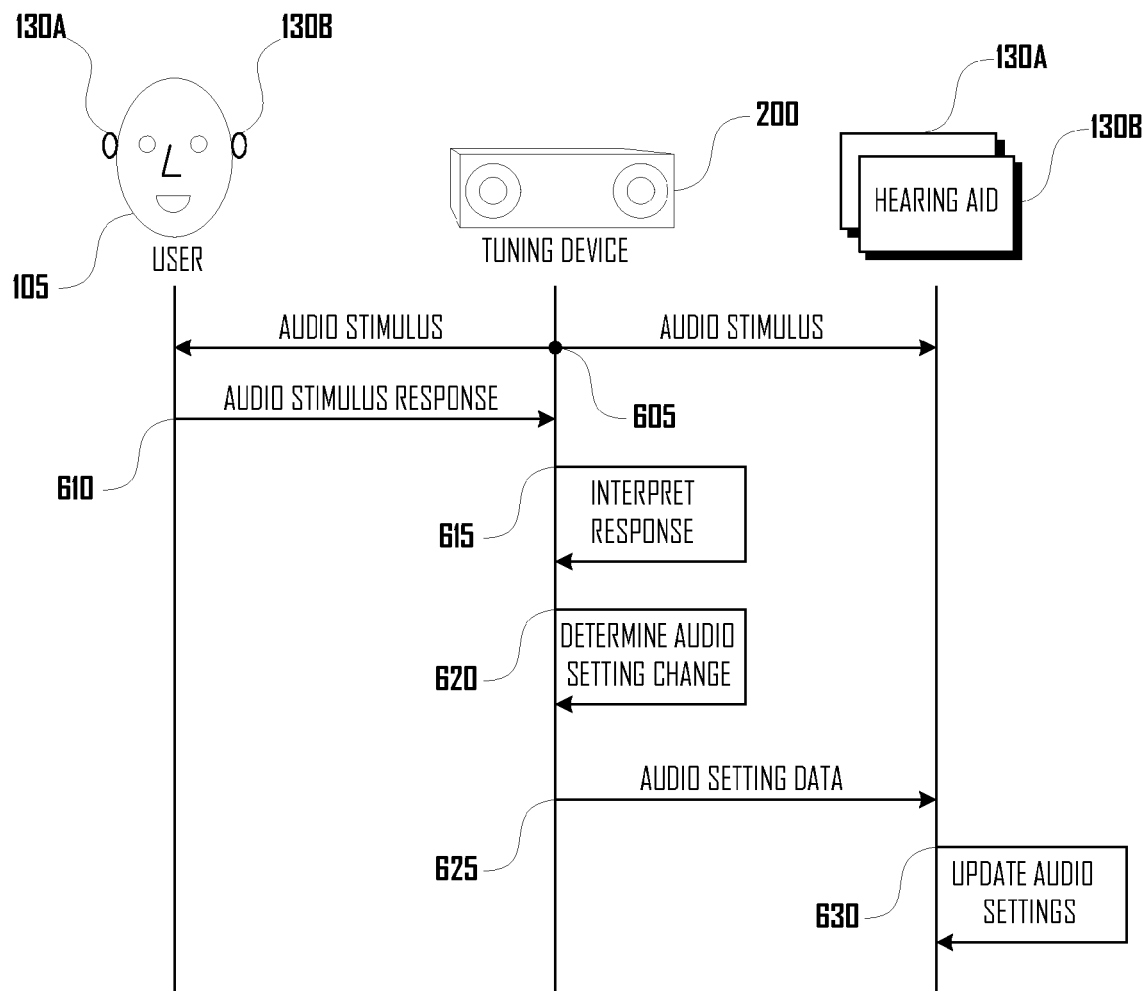
FIG. 6 is a diagram illustrating the actions taken by a first and second hearing aid, a tuning device, and a user wearing the first and second hearing aid in accordance with various embodiments.

FIG. 6 is a diagram illustrating the actions taken by a first and second hearing aid 130A-B, a tuning device 200, and a user 105 wearing the first and second hearing aid 130A-B. The actions begin where an audio stimulus is sent to the user 105 wearing the first and second hearing aid 130A-B. In various embodiments, the audio stimulus may be sent to the user 105 via calibrated transducers 235 of the tuning device 200.

Accordingly, sound waves 140 of the audio stimulus may propagate (i.e. be sent 605) through the air from the calibrated transducers 235 to the user 105, where the sounds waves 140 are received by the hearing aids 130A-B and perceived by the user 105. The user 105 therefore perceives the audio stimulus as the user 105 would normally perceive sound when wearing the hearing aids 130A-B.

In some embodiments, audio stimulus may be electronically sent 605 to first and/or second hearing aid 130A-B via first and/or second coupling body 135A-B, rather than being propagated through the air. A user may wish to have audio stimulus sent electronically in order to determine whether first and/or second hearing aid 130A-B is functioning properly (e.g., to verify that first and/or second hearing aid 130A-B is turned on and/or has a charged battery) or for other purposes.

Returning to the actions, an audio stimulus response is sent 610 to the tuning device 200, where the audio stimulus response is interpreted 615, and an audio setting change is determined 620. The tuning device 200 sends 625 audio setting data to the first and second hearing aid 130A-B, which updates 630 audio settings.

In various embodiments, a user 105 may submit 610 an audio stimulus response via an input device 120. Additionally, an audio stimulus response 610 may comprise an answer to a question about how the user 105 perceived the audio stimulus. For example a user 105 may be played an audio stimulus and the user 105 may receive a prompt such as "could you hear that clearly?"; "was the spoken word 'potato' or 'tomato' ?"; "did that sound tinny?"; "did that sound muddy?", or the like. A user 105 may provide a binary response (e.g. 'yes' or 'no'); a multiple choice response; or a freeform response (e.g. text or audio input).

In some embodiments a user 105 may respond to a "Goldilocks" query, and the like, as set out in U.S. patent application Ser. No. 13/889,217; titled HEURISTIC HEARING AID TUNING SYSTEM AND METHOD with inventors Daniel Wiggins and Donald Bowie, which is hereby fully incorporated by reference in its entirety.

Figure 7:
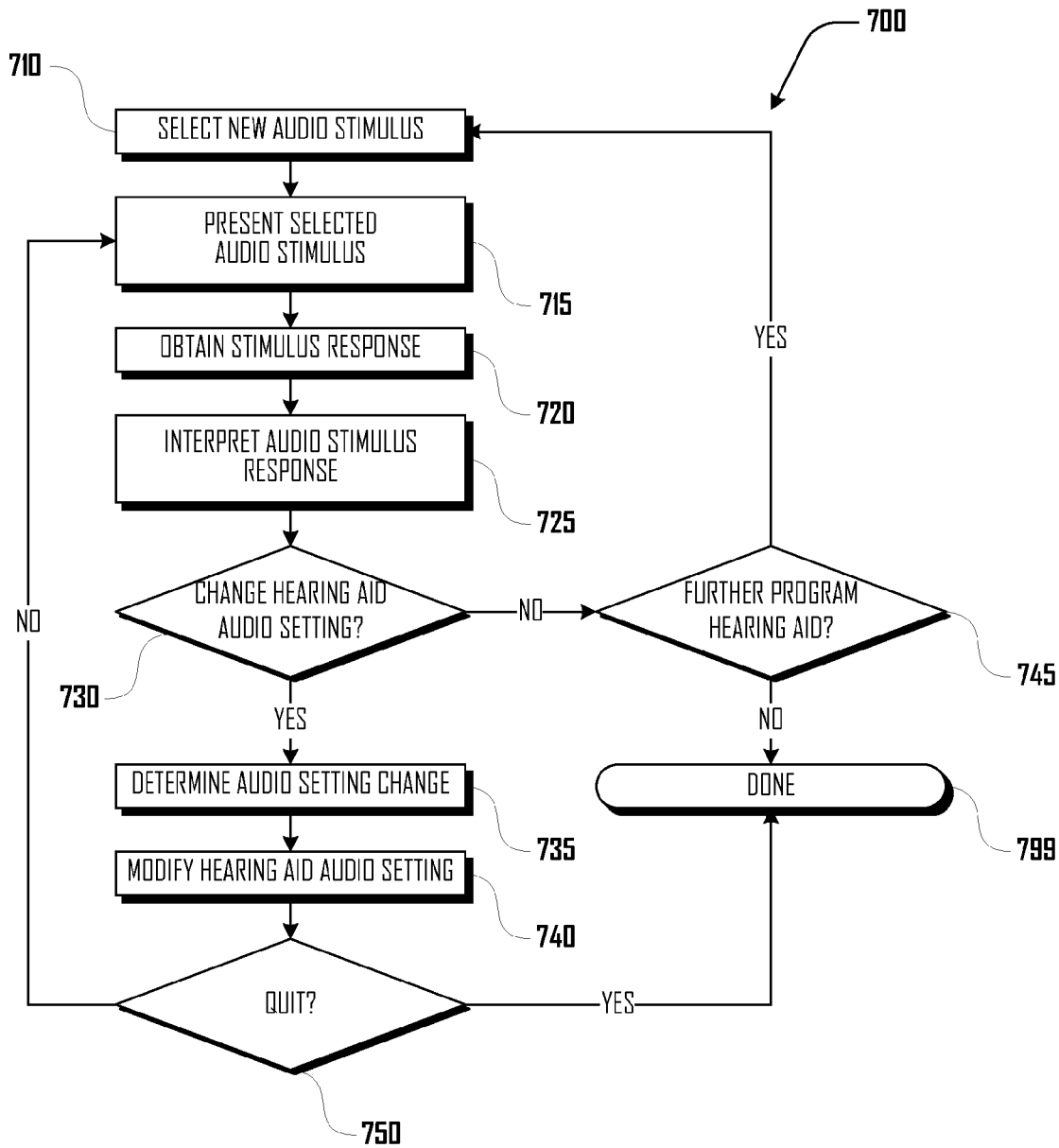
FIG. 7 is a flow diagram illustrating a hearing aid tuning routine in accordance with various embodiments.

FIG. 7 is a flow diagram illustrating a hearing aid tuning routine 700 in accordance with various embodiments. The hearing aid tuning routine 700 begins in block 710, where a new audio stimulus is selected. For example, an audio stimulus may be selected based on a problem identified by the user 105, or an audio stimulus may be selected based on a diagnostic routine. For example, if a user 105 indicates lack of vocal intelligibility, an audio stimulus relating to perception of vocal sounds such as 'm', 'b' or 'v' or vowels may be selected.

In block 715 the selected audio stimulus is presented, and in block 720, an audio stimulus response is obtained. In block 725 the audio stimulus response is interpreted. For example, if a user 105 provides an audio stimulus response that indicates that they are not perceiving vocal sounds such as 'm', 'b' or 'v', this may indicate that frequencies in the 2-4 KHz range should be reduced to improve vocal intelligibility.

In decision block 730, a determination is made whether to change a hearing aid audio setting. If it is determined to change a hearing aid audio setting, the hearing aid tuning routine 700 continues to block 735, where an audio setting change is determined. In block 740, the hearing aid audio setting is modified.

The hearing aid tuning routine 700 continues to decision block 750 where a determination is made whether the user 105 desires to quit. If so, then the hearing aid tuning routine 700 ends in block 799. However, if the user 105 does not desire to quit, then the hearing aid tuning routine 700 cycles back to block 715, where the selected audio stimulus is again presented.

Returning to decision block 730, if a determination is made that there is not a need to change a hearing aid audio setting, the hearing aid tuning routine 700 continues to decision block 745 where a determination is made whether to further program a hearing aid. If a determination is made not to further program a hearing aid, then the hearing aid tuning routine 700 continues to block 799, where the hearing aid tuning routine 700 is done.

However, if in decision block 745 a determination is made to further program a hearing aid, then the hearing aid tuning routine 700 cycles back to block 710, where a new audio stimulus is selected.

For example, where a user 105 indicates lack of vocal intelligibility of sounds such as 'm', 'b' or 'v', various frequencies in the 2-4 kHz range may be reduced or boosted in an attempt to improve vocal intelligibility. The same or a different audio stimulus may be played for the user 105 again, and the user's 105 stimulus response may or may not indicate that vocal intelligibility has improved. If it has not, for example, additional changes may be made to the settings of frequencies in the 2-4 kHz range, or other changes to other frequencies may be made. Such changes may be modified until the user 105 has obtained a desired audio response from the hearing aids 103A, 130B. Additionally, once a user 105 has resolved one issue relating to the audio response of the hearing aids 130A-B, the user 105 may choose to resolve additional issues related to hearing aid response, or the like.

Figure 8:
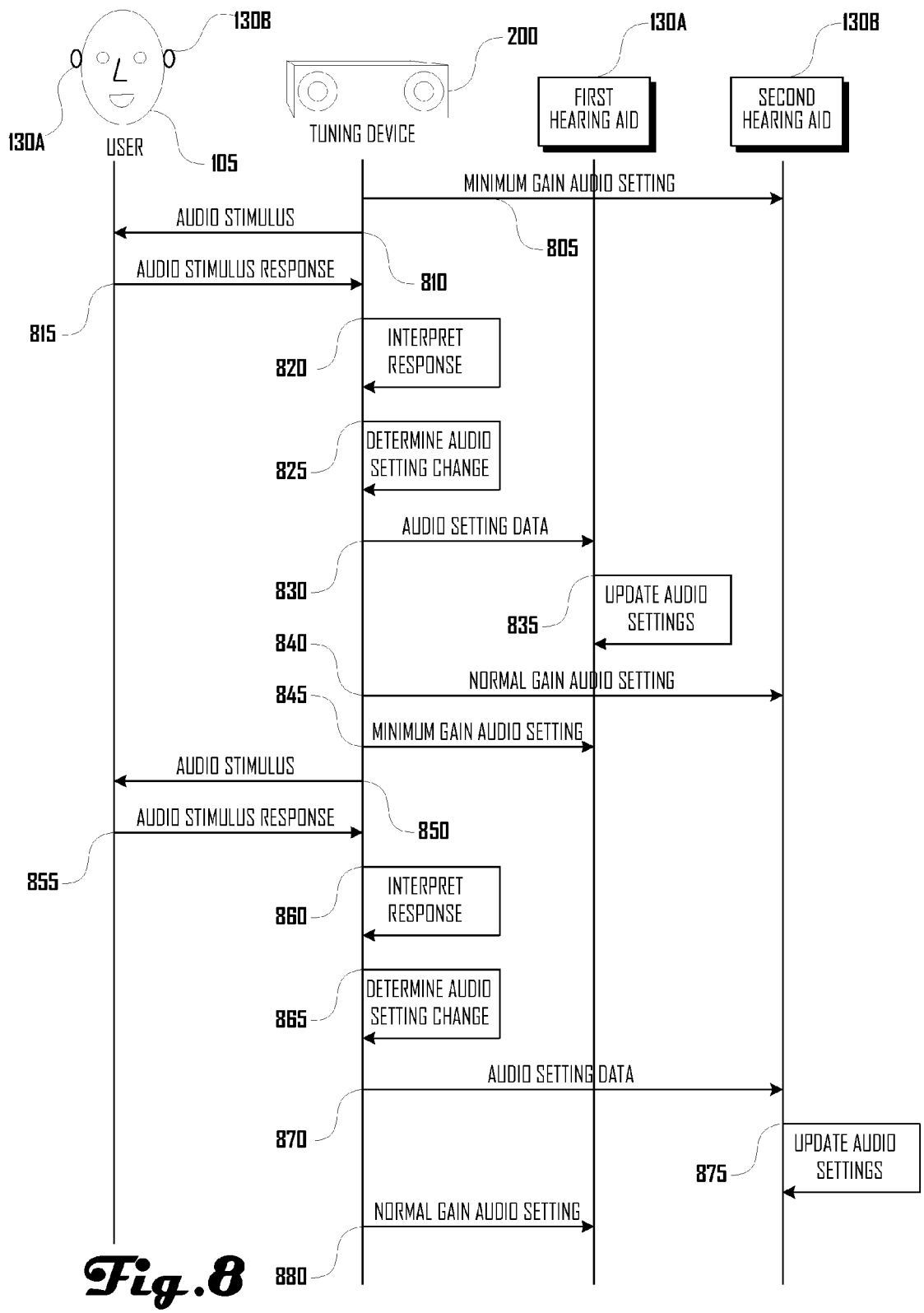
FIG. 8 is a diagram illustrating the actions taken by a first and second hearing aid and a tuning device in accordance with various embodiments.

FIG. 8 is a diagram illustrating the actions taken by a first and second hearing aid 130A-B, a tuning device 200, and a user 105 wearing the first and second hearing aid 130A-B. The actions begin where the tuning device 200 sends 805 a minimum gain audio setting to the second hearing aid 130B. For example, in various embodiments, it may be desirable to isolate a single hearing aid 130 during tuning so that the differences in a user's 105 ears can be accommodated. In such embodiments, one of a pair of hearing aids 130A-B may be set to zero gain, or may be switched off, or otherwise set so that the hearing aid 130 does not produce sound. Accordingly, the other hearing aid 130 may thereby be isolated.

Returning to the actions, the tuning device 200 sends 810 an audio stimulus to the user 105 wearing the first and second hearing aids 130A-B, and the user 105 sends 815 an audio stimulus response to the tuning device 200. As discussed herein, sending 810 an audio stimulus may comprise playing the audio stimulus via calibrated transducers 235.

The audio stimulus response is interpreted 820, and an audio setting change is determined 825. The tuning device 200 sends 830 audio setting data to the first hearing aid 130A, where audio settings are updated 835. The tuning device 200 then sends 840 a normal gain audio setting to the second hearing aid 130B and sends 845 minimum gain audio setting to the first hearing aid 130A. In various embodiments, a normal gain audio setting may be the gain setting that was present before the hearing aid 130 obtained a minimum gain audio setting, or may be various other gain settings.

The tuning device 200 then sends 850 an audio stimulus to the user 105 wearing the first and second hearing aid 130A-B and the user 105 sends 855 an audio stimulus response to the tuning device 200. The audio stimulus response is interpreted 860 and an audio setting change is determined 865. The tuning device 200 sends 870 audio setting data to the second hearing aid 130B where audio settings are updated 875. The tuning device 200 then sends 880 a normal gain audio setting to the first hearing aid 130A.

Figure 9:
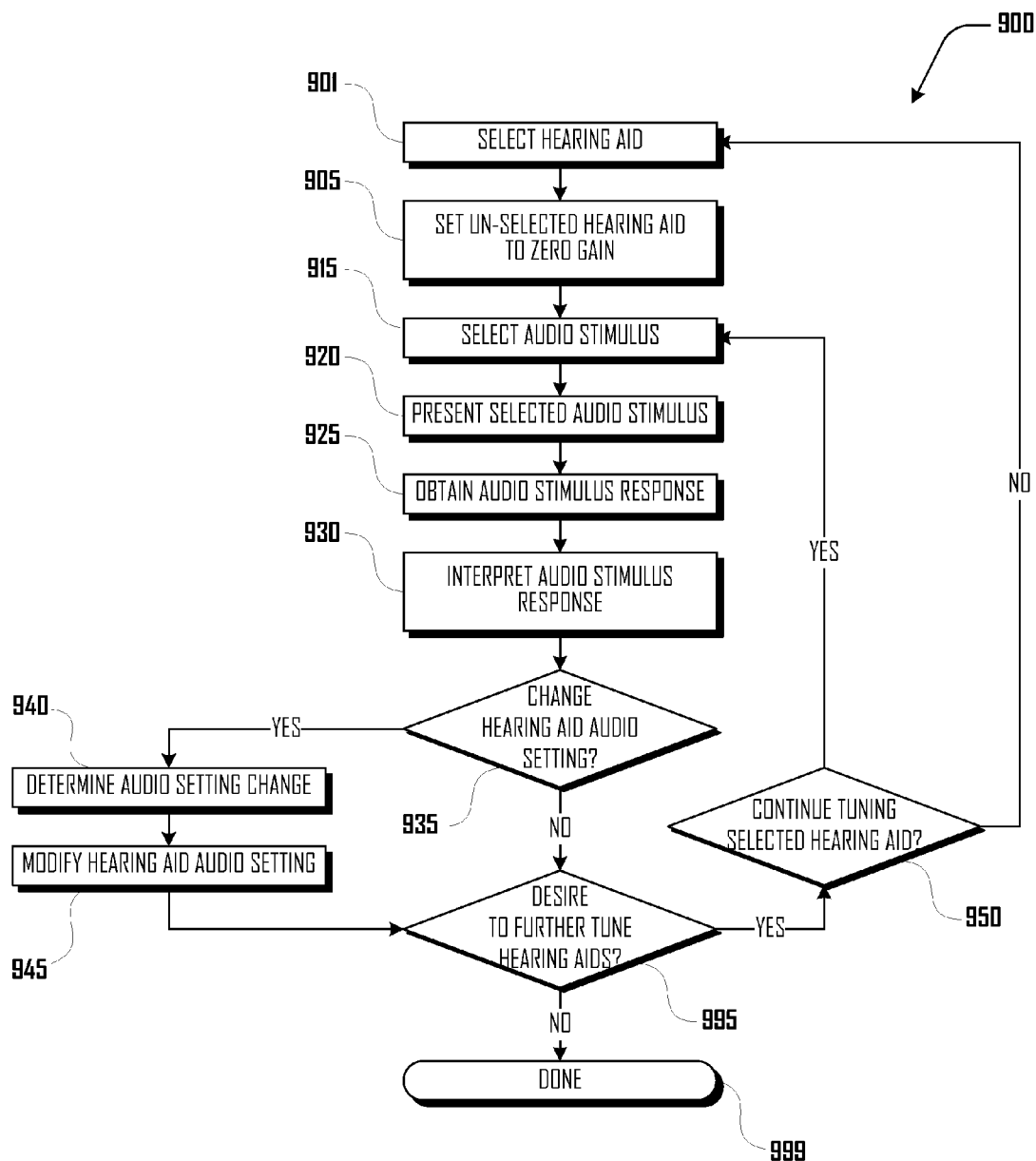
FIG. 9 is a flow diagram illustrating a first and second hearing aid tuning routine in accordance with various embodiments.

FIG. 9 is a flow diagram illustrating a first and second hearing aid tuning routine 900 in accordance with various embodiments. The first and second hearing aid tuning routine 900 begins in block 901, where a hearing aid is selected. For example user 105 may wish to isolate his or her first or second hearing aid 130A-B for tuning. In block 905, the un-selected hearing aid 130B is set to minimum gain, and in block 915 a new audio stimulus is selected. In block 920, the selected audio stimulus is presented, and in block 925, an audio stimulus response is obtained. In block 930, the audio stimulus response is interpreted.

In decision block 935, a determination is made whether there is a need to change a setting on the selected hearing aid audio. If so, the first and second hearing aid tuning routine 900 continues to block 940 where an audio setting change is determined, and in block 945, an audio setting is modified on the selected hearing aid 130A-B. First and second hearing aid tuning routine 900 then proceeds to decision block 995, discussed below.

Returning to decision block 935, if a determination is made not to change a hearing aid audio setting, then the first and second hearing aid tuning routine 900 continues to decision block 995, where a determination is made whether the user desires to continue first and second hearing aid tuning routine 900. If the user does not wish to continue, first and second hearing aid tuning routine 900 ends at block 999. If in decision block 995, the user indicates a desire to continue, first and second hearing aid tuning routine 900 proceeds to decision block 950, where a determination is made whether the user 105 desires to continue tuning the selected hearing aid. If the user 105 desires to continue tuning the selected hearing aid, then the first and second hearing aid tuning routine 900 cycles back to block 915, where a new audio stimulus is selected. In some embodiments, first and second hearing aid tuning routine 900 may instead cycle back to block 920, where the same audio stimulus may be presented to the user again.

If in decision block 950, the user indicates a desire to tune the other (un-selected) hearing aid, first and second hearing aid tuning routine 900 cycles back to block 901, where the other hearing aid is selected.

Figure 10A:
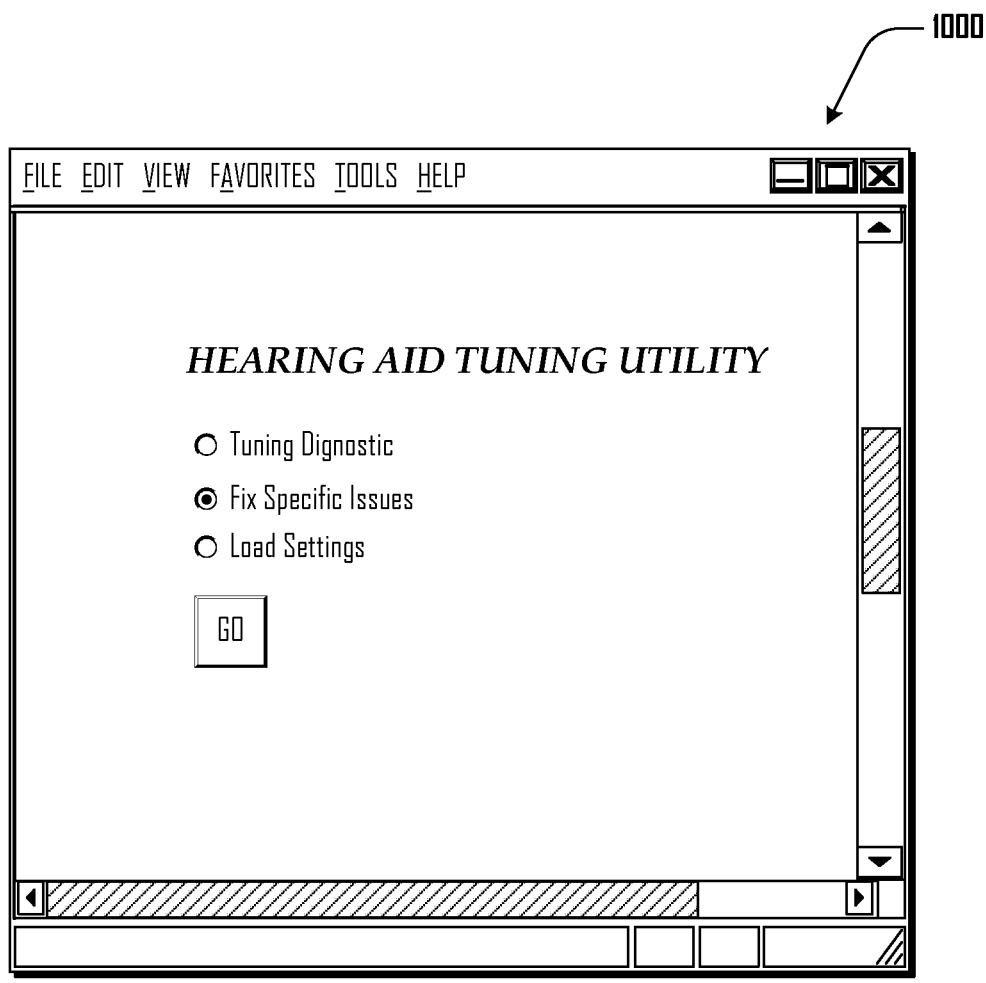
FIG. 10a is a hearing aid tuning graphic interface in accordance with an embodiment.
Figure 10B:
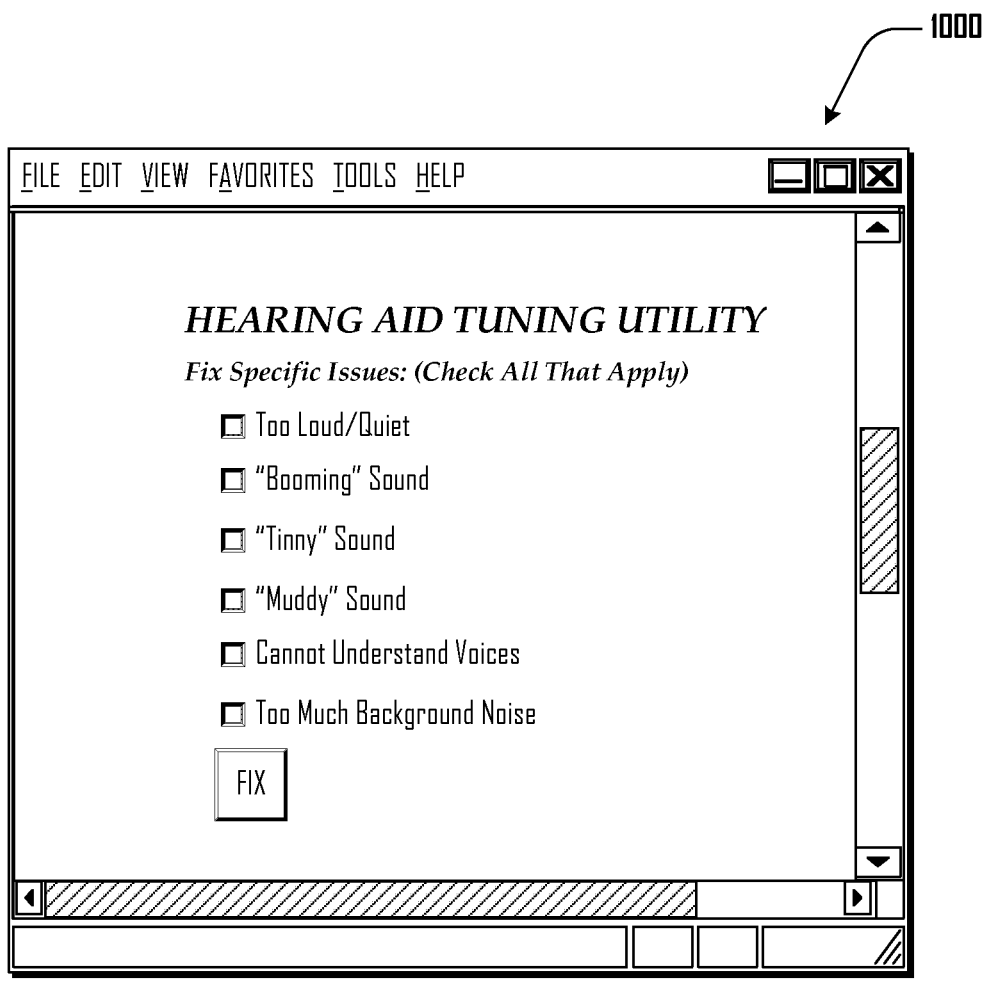
FIG. 10b is a hearing aid tuning graphic interface in accordance with another embodiment.
Figure 10C:
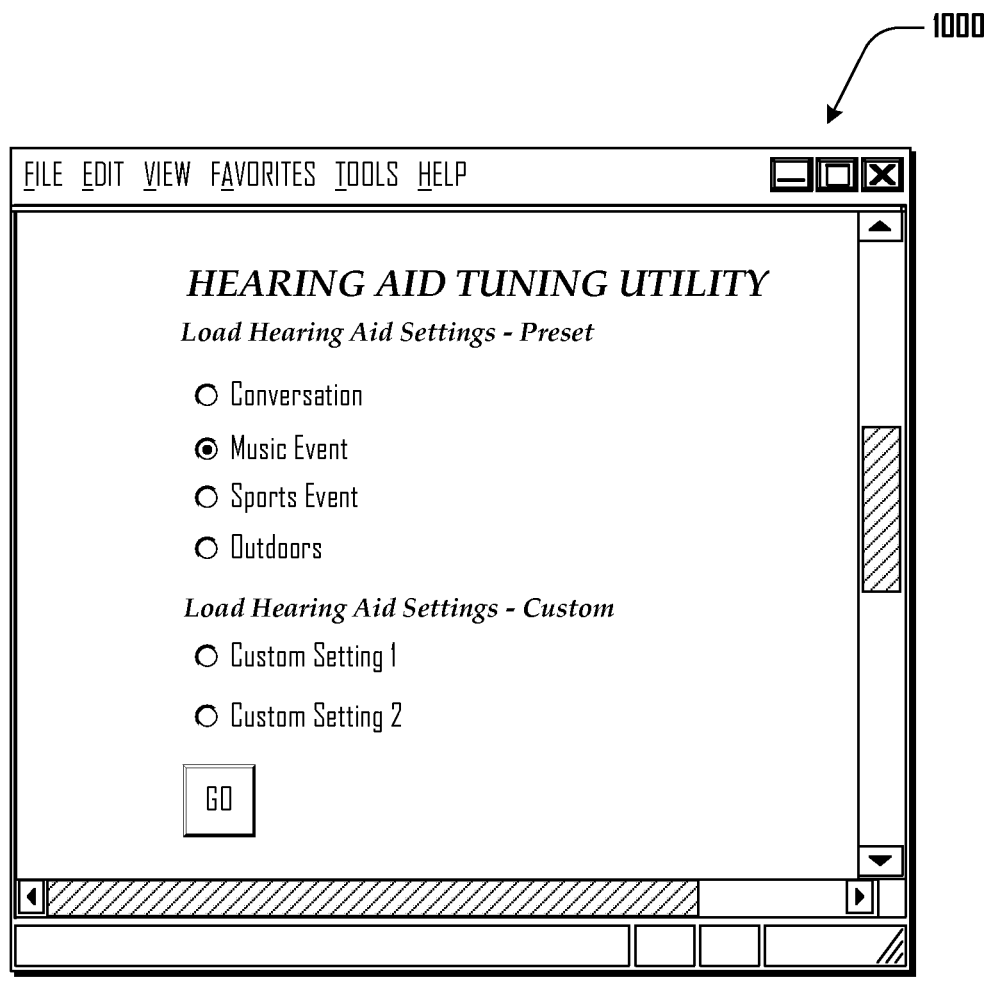
FIG. 10c is a hearing aid tuning graphic interface in accordance with a further embodiment.

FIGS. 10a-10c depict a hearing aid tuning graphic interface 1000 in accordance with various embodiments. For example, FIG. 10a depicts a hearing aid tuning graphic interface 1000 that allows a user 105 to select a tuning diagnostic routine, fix specific issues, or load various hearing aid settings.

FIG. 10b depicts a hearing aid tuning graphic interface 1000 wherein a user 105 may select specific issues to fix, issues that may relate to volume, undesirable audio characteristics (e.g. "booming", "tinny" or "muddy"), or other issues such as vocal intelligibility or too much background noise. In various embodiments, a user 105 may select various issues and be presented with one or more audio stimuli, which may diagnose and facilitate correction of selected issues.

FIG. 10c depicts a hearing aid tuning graphic interface 1000 wherein a user 105 may select various hearing aid settings, which may include preset or custom hearing aid settings. In some embodiments, these settings may be in relation to a current hearing aid setting or other hearing aid setting. In some embodiments, hearing aid settings can be modified by a user 105, or custom settings may be saved. For example, a user 105 may save hearing aid settings before modifying any such settings so that initial settings can be recovered if the user 105 desires.

Some exemplary preset hearing aid settings may include "conversation"; "music event"; "sports event"; "outdoors" and the like. For example, where a "conversation" setting is selected, frequency levels may be modified to increase voice intelligibility and to reduce the gain of frequencies outside of the vocal range. In some embodiments, settings relating to voice optimization may relate to persons of specific gender, age, identity, and the like.

Figure 11A:
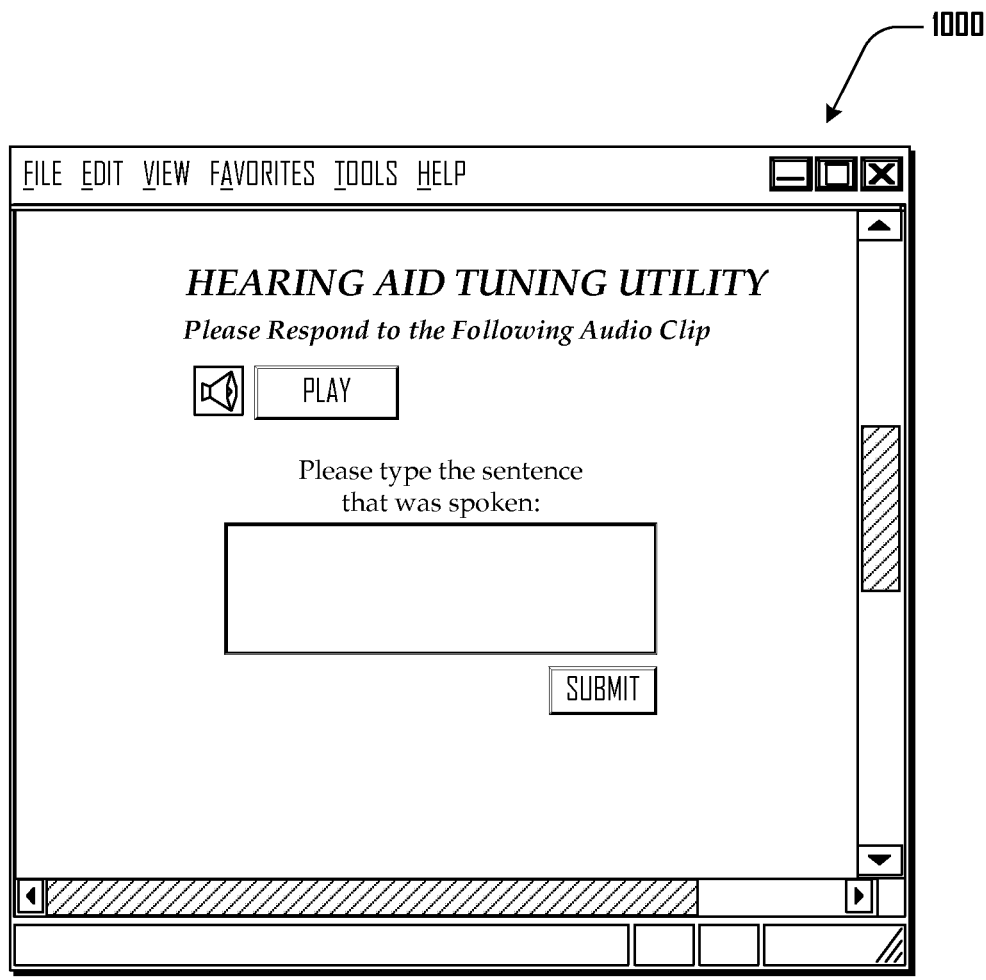
FIG. 11a is a hearing aid tuning graphic interface in accordance with an embodiment.
Figure 11B:
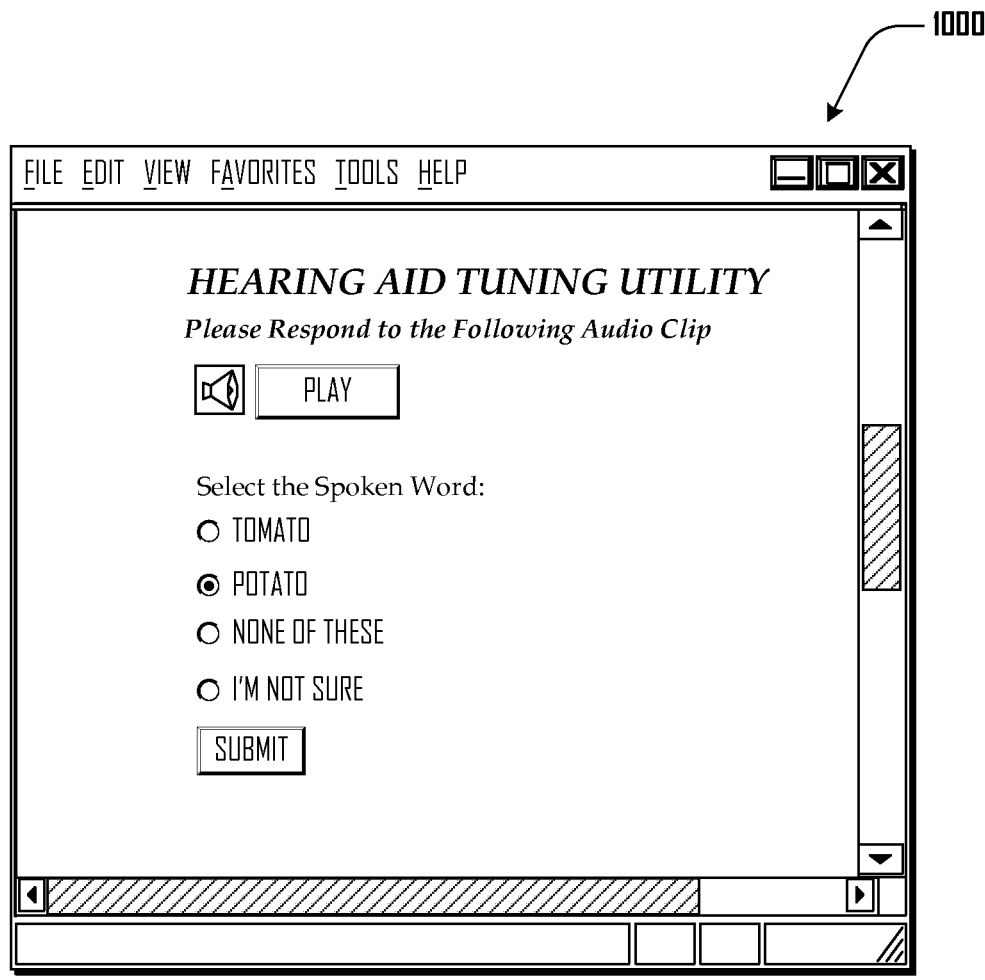
FIG. 11b is a hearing aid tuning graphic interface in accordance with another embodiment.
Figure 11C:
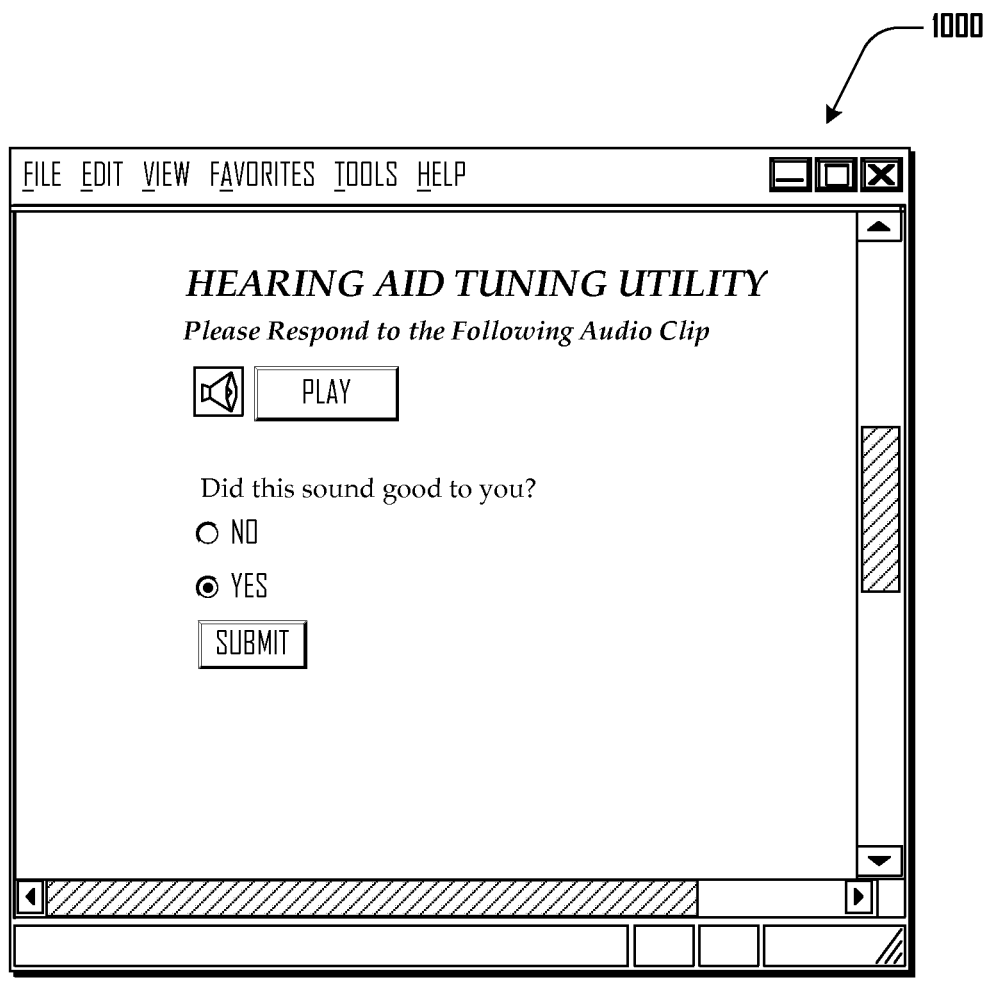
FIG. 11c is a hearing aid tuning graphic interface in accordance with a further embodiment.

FIGS. 11a-11d depict a hearing aid tuning graphic interface 1000 in accordance with various embodiments. FIG. 11a depicts a hearing aid tuning graphic interface 1000 where a user 105 may respond to an audio stimulus via text input. FIG. 11b depicts a hearing aid tuning graphic interface 1000 where a user 105 may respond to an audio stimulus via multiple choice response. FIG. 11c depicts a hearing aid tuning graphic interface 1000 where a user 105 may respond to an audio stimulus via a binary 'yes' or 'no' response.

Figure 11D:
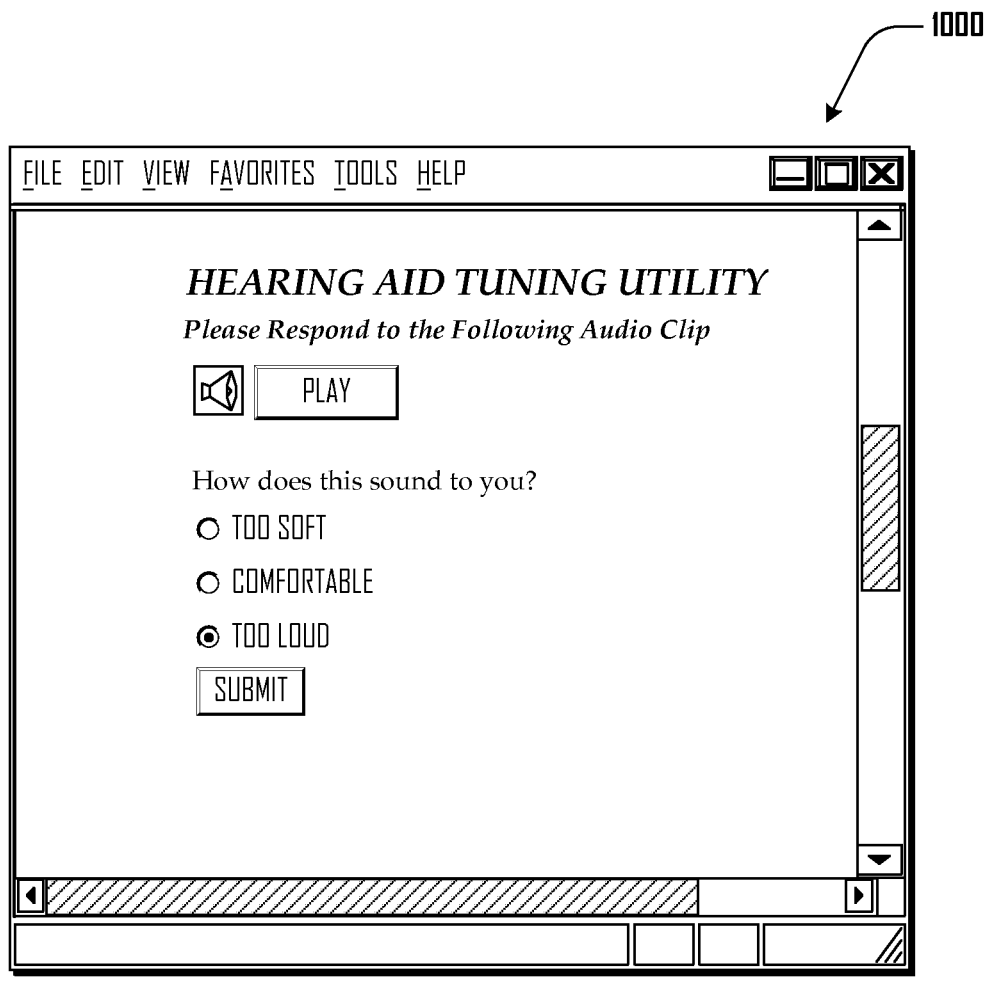
FIG. 11d is a hearing aid tuning graphic interface in accordance with a still further embodiment.

FIG. 11d depicts a hearing aid tuning graphic interface 1000 where a user 105 may respond to an audio stimulus via a "Goldilocks" response. For example, in some embodiments, a user 105 may respond to a "Goldilocks" query, and the like, as set out in U.S. patent application Ser. No. 13/889,217; titled HEURISTIC HEARING AID TUNING SYSTEM AND METHOD with inventors Daniel Wiggins and Donald Bowie, which is fully incorporated by reference in its entirety.

FIGS. 10a-10c and FIGS. 11a-11d each depict an exemplary hearing aid tuning graphic interface 1000; however, it should be clear that these exemplary hearing aid tuning graphic interfaces 1000 should not be construed to limit the great variety of hearing aid tuning graphic interfaces 1000 that are contemplated within the scope of various embodiments. For example, modes of input and graphic depictions thereof may be in any form that is operable to facilitate hearing aids 130A-B being tuned, tested, programmed, diagnosed, and the like.

Additionally, although specific embodiments have been illustrated and described herein, a wide variety of alternate and/or equivalent implementations may be substituted for the specific embodiments shown and described without departing from the scope of the embodiments described herein. This application is intended to cover any adaptations or variations of the embodiments discussed herein. While various embodiments have been illustrated and described, as noted above, many changes can be made without departing from the spirit and scope of the embodiments described herein.

We claim:

1. A tuning-device-implemented method for tuning a hearing aid worn by a wearer, the hearing aid having a plurality of programmatically adjustable settings, the tuning device comprising at least one coupling body, the method comprising:
  displaying, on a display associated with the tuning device, a first graphical user interface ("GUI") allowing the wearer to select one of a plurality of hearing aid issues;
  receiving first input, by the tuning device from the wearer via said first GUI, indicating a wearer-indicated hearing aid issue of said plurality of hearing aid issues;
  programmatically coupling, by the tuning device, with the hearing aid via said at least one coupling body;
  obtaining, by the tuning device, a plurality of current hearing-aid audio settings associated with the programmatically coupled hearing aid;
  selecting, by the tuning device, an audio stimulus of a plurality of audio stimuli based at least in part on said wearer-indicated hearing aid issue;
  presenting, by the tuning device to the wearer, said selected audio stimulus;
  selecting, by the tuning device according to at least one of said selected audio stimulus and said wearer-indicated issue, a second GUI soliciting wearer feedback related to presenting said selected audio stimulus;
  displaying said second GUI on said display;
  receiving second input, by the tuning device from the wearer via said second GUI, indicating said wearer feedback;
  automatically determining, by the tuning device, a change to at least one of said plurality of current hearing-aid audio settings according to said wearer feedback;
  programmatically adjusting, by the tuning device, said at least one of said plurality of current hearing-aid audio settings.

2. The method of claim 1, wherein obtaining said plurality of current hearing-aid audio settings comprises requesting said plurality of current hearing-aid audio settings from the programmatically coupled hearing aid.

3. The method of claim 1, wherein obtaining said plurality of current hearing-aid audio settings comprises retrieving said plurality of current hearing-aid audio settings from a user-data database associated with the tuning device.

4. The method of claim 3, further comprising storing said adjusted at least one of said plurality of current hearing-aid audio settings in said user-data database.

5. The method of claim 1, further comprising:
  programmatically coupling, by the tuning device, with a second hearing aid worn by the wearer via a second coupling body of said at least one coupling body; and
  programmatically isolating the hearing aid worn by the wearer from said second hearing aid prior to presenting said selected audio stimulus.

6. The method of claim 5, wherein isolating the hearing aid comprises a selected one of programmatically adjusting a gain setting of said second hearing aid to a minimum-gain setting and programmatically switching said second hearing aid off.

7. The method of claim 1, wherein presenting said selected audio stimulus comprises propagating said selected audio stimulus as sound waves via at least one calibrated transducer associated with the tuning device.

8. The method of claim 7, wherein said selected audio stimulus comprises a spoken sentence, and wherein said second input comprises text entered by the wearer corresponding to the wearer's perception of said spoken sentence.

9. The method of claim 7, wherein said selected audio stimulus comprises a spoken word, wherein said second GUI allows the wearer to select one of a plurality of spoken words, and wherein said second input comprises an indication of a selected word of said plurality of spoken words, said selected word corresponding to the wearer's perception of said spoken word.

10. The method of claim 7, wherein said second GUI allows the wearer to select one of at least two choices, and wherein said second input comprises an indication of a selected choice of said at least two choices, said selected choice corresponding to the wearer's perception of said audio stimulus.

11. A hearing aid tuning system comprising:
  a tuning device having at least one coupling body, the tuning device operable to:
    allow a wearer of a hearing aid to indicate one of a plurality of hearing aid issues as first input via a first graphical user interface ("GUI") with the tuning device programmatically coupled with the hearing aid via the at least one coupling body of the tuning device;
    obtain a plurality of current hearing aid audio settings associated with the hearing aid;
    select an audio stimulus of a plurality of audio stimuli based at least in part on said one of the plurality of hearing aid issues;
    present said audio stimulus to the wearer;
    select, according to at least one of said audio stimulus of the plurality of audio stimuli or said one of the plurality of hearing aid issues, a second GUI in soliciting wearer feedback related to presenting said audio stimulus;
    present said second GUI on a display;
    receive second input via said second GUI indicating said wearer feedback; and
    automatically determine and perform a change to at least one of said plurality of current hearing aid audio settings as a programmatic adjustment according to said wearer feedback.

12. The system of claim 11, further comprising:
  the display, operable to present said first and second graphic user interfaces allowing said wearer to at least select a hearing-aid tuning routine in indicating said one of the plurality of hearing aid issues and indicate said wearer feedback as a response to said audio stimulus.

13. The system of claim 11, further comprising:
  said hearing aid, programmatically coupled with said tuning device.

14. The system of claim 11, wherein said tuning device comprises:
  a communication interface operable to connect to a host device.

15. The system of claim 11, wherein said at least one coupling body comprises:
  a magnetic-inductive data coupler.

* * * * *